United States Patent [19]
Brasile

[11] Patent Number: 6,024,698
[45] Date of Patent: Feb. 15, 2000

[54] APPARATUS FOR MONITORING FUNCTIONAL CHARACTERISTICS OF AN ORGAN INTENDED FOR TRANSPLANTATIONS

[75] Inventor: Lauren Brasile, Albany, N.Y.

[73] Assignee: Breonics, Inc., Schenectady, N.Y.

[21] Appl. No.: 08/992,284

[22] Filed: Dec. 17, 1997

Related U.S. Application Data

[60] Division of application No. 08/670,569, Jun. 26, 1996, Pat. No. 5,699,793, which is a continuation-in-part of application No. 08/246,801, May 20, 1994, abandoned.

[51] Int. Cl.[7] .................................................. G01N 27/26
[52] U.S. Cl. ............................................................. 600/300
[58] Field of Search ..................................... 600/300, 309, 600/310, 345, 365; 128/897, 898; 604/4–6, 7

[56] References Cited

U.S. PATENT DOCUMENTS

| | | | |
|---|---|---|---|
| 4,109,505 | 8/1978 | Clark et al. ................................ | 73/1 R |
| 4,786,394 | 11/1988 | Enzer et al. .............................. | 204/401 |
| 4,798,824 | 1/1989 | Belzer et al. .............................. | 514/60 |
| 4,920,044 | 4/1990 | Bretan, Jr. .................................. | 435/1 |
| 4,935,000 | 6/1990 | Dudek ....................................... | 600/36 |
| 5,385,539 | 1/1995 | Maynard ..................................... | 604/4 |
| 5,685,988 | 11/1997 | Malchesky ............................... | 604/4 X |

*Primary Examiner*—Samuel Gilbert
*Attorney, Agent, or Firm*—Heslin & Rothenberg, P.C.

[57] ABSTRACT

The present invention is directed to a device useful for measuring functional characteristics of an organ being perfused at near normal metabolism using an ex vivo warm preservation process/system. The device comprises means for diverting from the flow lines of the warm preservation system a small sample of perfusate which has already circulated through the organ, and means for collecting the perfusate that measurements can be performed. The functional characteristics include parameters reflecting organ metabolism measured from perfusate which has circulated through the organ, from organ product produced and collected from the organ, or from both the circulated perfusate and the collected organ product during the warm preservation process/system. The measured parameters may then be compared to reference intervals as a method of prospectively assessing functional capabilities of the organ posttransplantation.

6 Claims, 4 Drawing Sheets

APPARATUS FOR MONITORING FUNCTIONAL CHARACTERISTICS OF AN ORGAN INTENDED FOR TRANSPLANTATIONS

This application is a division of U.S. patent application Ser. No. 08/670,569, filed Jun. 26, 1996 now issued as U.S. Pat. No. 5,699,793, which was a continuation-in-part of U.S. patent application Ser. No. 08/246,801 filed May 20, 1994, now abandoned, the disclosure of which is incorporated herein by reference.

BACKGROUND OF THE INVENTION

1. Field of the Invention

This invention relates to a novel method for monitoring functional characteristics of an organ/tissue ("organ"), being stored in an ex vivo warm preservation process, intended for transplantation. More particularly, the method involves measuring one or more indicia of the organ function, as a means of assessing functional capabilities of the organ which can then be correlated with its posttransplantation course.

2. Description of the Background and Related Art

There continues to be an extreme shortage of organs for transplantation. For example, kidney transplantation is largely dependant upon the availability of organs retrieved from heart-beating cadaver donors. While awaiting transplantation, kidneys must be stored in a fashion that will result in the restoration of normal, immediate function. Therefore, the clinical preservation of organs is much more limited than the experimental models.

Additionally, a large and as yet untapped source of organs for transplantation are accident victims who succumb at the site of an injury and those having short post-trauma survival times. These accident victims are not used as organ donors because of the ischemic damage. Likewise, older potential donors are often considered borderline because of questions relating to organ function. Thus, the development of methods which will allow clinicians to evaluate prospectively the functional capabilities of an allograft ex vivo may allow for the expansion of the organ donor pool. Similarly, the current demand for organs cannot be met with existing technology. Unless new sources of organs can be developed, the number of transplantation procedures will remain constant. Additionally, the donor pool cannot be substantially expanded because there is no process/system available to evaluate if the borderline or warm ischemically damaged organ will function when transplanted; i.e. until now, the only means to evaluate the functional capabilities of an organ intended for transplantation was to transplant it.

There are two commonly used methods of storage for kidneys—both involving hypothermia: preservation by continuous hypothermic perfusion; and simple hypothermic storage (see for example Collins et al., 1969, Lancet 2:1219). While a variety of perfusates have been utilized clinically, these two methods of kidney storage have remained substantially unchanged for the past 20 years. The current perfusate solution that represents the state-of-the-art in hypothermic organ preservation, and provides for optimized organ preservation under hypothermic conditions, contains components which prevent hypothermic induced tissue edema; metabolites which facilitate organ function upon transplantation; anti-oxidants; membrane stabilizers; colloids; ions; and salts (Southard et al.,1990, *Transpl.* 49:251; and Southard, 1989, *Transpl. Proc.* 21:1195). The formulation of this perfusate is designed to preserve the organs by hypothermic induced depression of metabolism. While it minimizes the edema and vasospasm normally encountered during hypothermic storage, it does not provide for the utilization of a substantially expanded donor pool. This is due to the fact that an allograft, marginally damaged by warm ischemia cannot tolerate further damage mediated by the hypothermia.

Further, since preservation of organs using hypothermia reduces organ metabolism and oxidative needs, such preservation methods do not allow for measurement of functional characteristics which can be used prospectively to determine the function of the organ posttransplantation. For example, while at normal physiologic temperatures the phospholipids making up the cell membranes are highly fluid, under the hypothermic conditions utilized to preserve organs intended for transplantation, the lipid bilayer experiences a phase-change and becomes gel-like, with greatly reduced fluidity. The essentially frozen lipid in the cell membranes negates the utilization of $O_2$, even in the presence of a high $O_2$-tension. The metabolic consequence is glycolysis, which is analogous to the state of anoxia. The hypothermic conditions utilized in organ preservation probably represents the reason why previous studies raising the $O_2$-tension did not uniformly demonstrate the benefit of increased oxygenation of tissues.

In organ metabolism, a direct relationship between oxygen requirements and temperature exists. In fact, hypothermia may exert a greater depression of oxidative metabolism in the kidney than in the body as a whole and may even help to explain the success in preserving kidney relative to other organs. A major portion of the oxygen consumed by the kidney is utilized for the process of active sodium reabsorption and reabsorption is by far the most important of all the tubular transport processes (Zerahn, 1956, *Phsiol. Scand.* 36:300). It has been described that below 18° C., hypothermia inhibits the tubular activity of the kidney (Bickford et al., 1937, *J. Physiol.* 89:198) and that at 4° C., the utilization of oxygen is approximately 5% of that at normothermia.

Hypothermic storage can further complicate assessment of function since it is not benign; i.e., it can produce vasospasm and subsequent edema in an allograft (Robison, 1953, *Biol. Rev.* 28:153; Rixon et al., 1954, *Rev. Canc. Biol.* 13:83). Hypo-thermically preserved organs can experience glomerular endothelial cell swelling and loss of vascular integrity along with tubular necrosis. These phenomenon can be attributed to the hypothermic conditions employed. Hypothermia can also inhibit the Na/K dependant ATPase and result in the loss of the cell volume regulating capacity. The loss of volume regulation is what causes the cellular swelling and damage. Without adequate oxygen delivery, the anoxia leads to disintegration of the smaller vessels after several hours of perfusion. The inability to adequately utilize oxygen, and the subsequent depletion of ATP stores, mean that anaerobic glycolysis is the principal source of energy under traditional preservation conditions. The lack of molecular oxygen for oxidative phosphorylation which occurs in either warm or cold ischemia, leads to the accumulation of NADH and the depletion of ATP stores within the mitochondria. The subsequent loss of nucleosides is probably a very important factor in the failure of tissues subjected to warm ischemia and prolonged periods of cold ischemia to regen- erate ATP after restoration of the blood supply. The inability to supply adequate oxygen has lead to the routine reliance on hypothermia for organ preservation.

Recently, processes/systems have been described which utilize a temperature range of 18° C.–35° C. for some form of organ preservation. However, none of these have established organ metabolism or function anywhere near the normal range. Nor have any of these described using the product of the organ metabolism during storage ex vivo or in situ, to establish functional capabilities which can be correlated with posttransplantation course.

The present inventor has developed a process/system to preserve organs ex vivo without traditional hypothermia (4° C.–10° C.) which has been described in detail previously (U.S. patent application Ser. Nos. 08/476,456 and 08/372,782, the disclosures of which are herein incorporated by reference). The process/system provides the necessary oxygen delivery, nutrients for metabolism, oncotic pressure, pH, perfusion pressures, and flow rates to support organ metabolism ex vivo, most often within or near the respective normal range in vivo. A near normal rate of metabolism is defined herein as about 70%–90% of the range of normal rates of metabolism. Further, the process/system supports a level of metabolism ex vivo which provides enough oxidative metabolism to result in the normal functional product of the organ. The development of this process/system which supports organs ex vivo, without traditional hypothermia, presents the opportunity to support a near normal rate of metabolism.

SUMMARY OF THE INVENTION

All organ preservation processes/systems currently being used depend on severe hypothermia (4° C.–10° C.) to reduce the organ metabolism and oxidative needs. The hypothermia inhibits the organ metabolism by 95% and is the reason why organ function cannot be determined prospectively ex vivo. Therefore, such methods prevent assessing the function of an ex vivo organ relative to its course posttransplantation, because metabolic functions are mandatorily inhibited by the hypothermia employed. The few attempts at using a process/system to support organs ex vivo without severe hypothermia, have not reported that organ metabolism was achieved at a level which allowed for the functional product of the organ; i.e. approaching a near normal rate of metabolism in vivo.

The warm preservation technology developed by the present inventor has been described in detail previously in U.S. patent application Ser. Nos. 08/372,782 and 08/476,456) supports a level of metabolism ex vivo within or near the respective normal range in vivo and which provides enough oxidative metabolism to result in the normal functional product of the organ. For example, a renal allograft stored ex vivo via this process/system supports renal metabolism within a normal range and results in its normal functional product, namely urine. This production of urine during the process/system of warm ex vivo preservation presents the unique opportunity to prospectively determine the potential function of an allograft. Until now, the only means to evaluate the functional capabilities of an allograft was to transplant it.

Thus, in accordance with one aspect of the present invention, a method is disclosed to prospectively determine the potential function of an organ intended for transplantation.

In another aspect of the invention, a method to prospectively determine the potential function of an organ posttransplantation is disclosed, wherein by measuring functional characteristics related to organ metabolism while the organ is being perfused in an ex vivo warm preservation process/system at near normal rate of metabolism by measuring parameters of organ product or circulated perfusate during ex vivo warm preservation; values of the measured parameters can be compared to reference interval values (an established normal range) such that a value of one or more measured parameters outside the reference intervals may be indicia of organ damage, injury, or poor functional capabilities which may affect the function of the organ posttransplantation.

In a further aspect of the invention, wherein the organ intended for transplantation is a kidney, functional capabilities can be assessed by measuring parameters including, but not limited to, urine concentrations of protein, glucose, and creatinine; urine pH, osmolality, and specific gravity; kidney vascular flow rate, oxygen consumption, and glucose utilization (as measured from the perfusate).

In yet another aspect of the invention, wherein the organ intended for transplantation is a liver, functional capabilities can be assessed by measuring parameters including, but not limited to, bile concentrations of bile salts, cholesterol, alkaline phosphatase; bile pH; and liver vascular flow rate, oxygen consumption, and glucose utilization (as measured from the perfusate).

In another aspect of the invention, wherein the organ intended for transplantation is a pancreas, functional capabilities can be assessed by measuring parameters including, but not limited to, pancreatic enzyme concentrations such as amylase, lipase; the hormone insulin; pancreatic secretion pH, sodium and potassium; and pancreas vascular flow rate, oxygen consumption, and glucose utilization (as measured from the perfusate).

In another aspect of the invention, wherein the organ intended for transplantation is a heart, functional capabilities can be assessed by measuring parameters including, but not limited to, heart enzymes such as transaminases (aspartate aminotransferase, AST), lactate dehydrogenase (LD), fructose 1,6-diphosphate aldolase (ALS), malate dehydrogenase (MD), glutathione reductase (GR), creatine phosphokinase (CPK), hydroxybutyrate dehydrogenase (HBD); heart vascular flow rate, oxygen consumption, and glucose utilization (as measured from the perfusate). Other parameters include measuring the heart electric potential by electrocardiogram (ECG).

In a further aspect of the invention, wherein the organ intended for transplantation is a small bowel, functional capabilities can be assessed by measuring parameters including, but not limited to, functional assays such as gastric acid stimulation tests, and absorption assays using tracer molecules; small bowel vascular flow rate, oxygen consumption, and glucose utilization (as measured from the perfusate).

The above-discussed features, and attendant advantages of the present invention will become apparent by reference to the following detailed description when considered in conjunction with the accompanying figures.

DETAILED DESCRIPTION OF THE INVENTION

Figure 1:
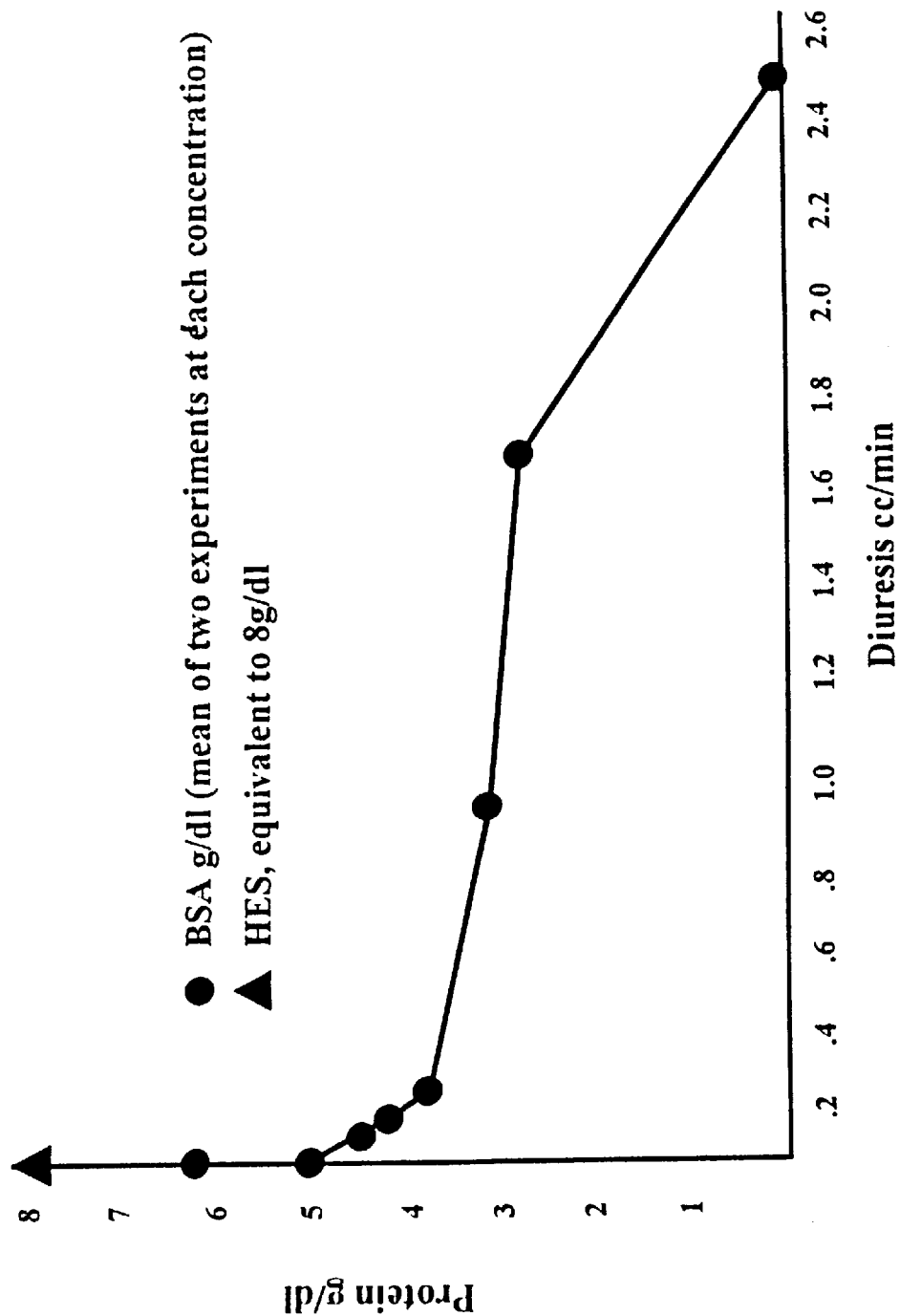
FIG. 1 is a graph representing the effect of protein (bovine serum albumin; "BSA",●) concentration on diuresis of kidneys using the ex vivo warm preservation process/system.

A transplantable organ is herein defined as an organ including, but not limited to kidney, heart, liver, lung, small bowel, pancreas, and eye. The present invention is related to warm preservation technology in which an organ is perfused at temperatures in the range of 18° C. to 35° C. with a perfusate composed of a highly enriched and modified tissue culture medium which is supplemented with an oxygen carrier such as a perfluorochemical emulsion. The process/system involves preserving the organ ex vivo with ongoing metabolic activity using a laminar or pulsatile pumping system. Thus, the process/system provides necessary oxygen delivery, nutrients for metabolism, oncotic pressure, pH, perfusion pressures, and flow rates to support organ metabolism ex vivo, most often within or near the respective normal range of metabolism in vivo. The metabolism of the organ is monitored ex vivo by assessing functional characteristics such as by determining perfusion pressures, flow rates, oxygen consumption, pH, osmolarity and glucose utilization. Additionally, product(s) of the organ metabolism can be collected and analyzed, without significantly altering the perfusion process, to prospectively assess organ function before transplantation.

EXAMPLE 1

Summary of Warm Preservation Technology

A process and compositions for preserving organs ex vivo without traditional hypothermia (4° C.–10° C.) has been described in detail previously (U.S. patent application Ser. Nos. 08/372,782 and 08/476,456, the disclosures of which have been incorporated by reference). The process provides the necessary oxygen delivery, nutrients for metabolism, oncotic pressure, pH, perfusion pressures, and flow rates to support organ metabolism ex vivo for at least up to 18 hours.

The hyperosmolar solution which may be used as a preservation solution for the initial organ flushing, and/or as a perfusate for storage of organs using a warm preservation technology (18° C.–35° C.) without extreme hypothermia. The perfusate has been designed to support the nutritional and metabolic needs of the vascular endothelium within a graft, thereby maintaining the integrity of the vasculature and subsequently the normal permeability of the organ. Among the components may be amino acids, ions, physiologic salts, impermeants, serum, serum proteins, sugars, lipids, attachment factors, growth factors, mucopolysaccharides, and an oxygen carrier. This is the first perfusate to be able to preserve organs without concomitant extreme hypothermia; and was specifically designed to potentiate the simultaneous growth of microvessel and large vessel endothelial cells; to support the integrity of vascular endothelium within a graft; and to support more normal permeability, and metabolism without extreme hypothermia. The preservation solution employs a cell culture-like basal medium, to which is added a variety of supplements which may include serum albumin as a source of protein and colloid; trace elements to potentiate viability and cellular function; pyruvate and adenosine for oxidative phosphorylation support; transferrin as an attachment factor; insulin and sugars for metabolic support; glutathione to scavenge toxic free radicals; cyclodextrin as a source of impermeant, scavenger, and potentiator of cell attachment factors; a very high $Mg^{++}$ concentration for microvessel metabolism support; mucopolysaccharides, comprising primarily chondroitin sulfates, for growth factor potentiation and hemostasis; a factor for promoting growth of endothelial cells acidic-fibroblast growth factor as a source of colloid, impermeant and growth promoter; and an oxygen carrier to support oxidative metabolism during metabolic function. As a result, the preservation solution has been found to preserve organs without extreme hypothermia, and does not present the common problems encountered with cold storage perfusates- namely edema, vasospasm, depletion of ATP stores, shutdown of ion pumps, glycolysis, and the generation of cold-induced toxic free radical intermediates. Although the composition of the preservation solution, for use with a warm preservation technology, can vary by constituent and constituent ranges as previously described, a preferred formulation is set forth below in Table 1 for purposes of illustration and not limitation.

TABLE 1

A PREFERRED COMPOSITION OF THE PRESERVATION SOLUTION

| | |
|---|---|
| DL-Alanine | .12 g/L |
| L-Arginine HCl | .14 g/L |
| DL-Aspartic Acid | .12 g/L |
| L-Cysteine $HCL.H_2O$ | .00022 g/L |
| L-Cystine 2HCl | .052 g/L |
| DL-Glutamic Acid | .2672 g/L |
| L-Glutamine | .2 g/L |
| Glycine | .1 g/L |
| L-Histidine $HCl.H_2O$ | .04376 g/L |
| L-Hydroxyproline | .02 g/L |
| DL-Isoleucine | .08 g/L |
| DL-Leucine | .24 g/L |
| L-Lysine HCl | .14 g/L |
| DL-Methionine | .06 g/L |
| DL-Phenylalanine | .10 g/L |
| L-Proline | .08 g/L |
| DL-Serine | .10 g/L |
| DL-Threonine | .12 g/L |
| DL-Tryptophan | .04 g/L |
| L-Tyrosine.2Na | .11532 g/L |
| DL-Valine | .10 g/L |
| Adenine Hemisulfate | .02 g/L |
| Adenosine Triphosphate.2Na | .002 g/L |
| Adenylic Acid | .0004 g/L |
| Alpha Tocopherol Phosphate.2Na | .00002 g/L |
| Ascorbic Acid | .0001 g/L |
| D-Biotin | .00002 g/L |
| Calciferol | .0002 g/L |
| Cholesterol | .0024 g/L |
| Choline Chloride | .001 g/L |
| Deoxyribose | .001 g/L |
| Folic Acid | .00002 g/L |
| Glutathione (Reduced) | .0001 g/L |
| Guanine HCl | .0006 g/L |
| Hypoxanthine | .0006 g/L |
| Menadione (Na Bisulfite) | .00003 g/L |
| Myo-Inositol | .0001 g/L |
| Niacinamide | .00005 g/L |
| Nicotinic Acid | .00005 g/L |
| PABA | .0001 g/L |
| D-Pantothenic Acid Ca | .00002 g/L |
| Polyoxyethylenesorbitan Monooleate | .04 g/L |
| Pyridoxal HCl | .00005 g/L |
| Pyridoxine HCl | .00005 g/L |

TABLE 1-continued

A PREFERRED COMPOSITION OF THE PRESERVATION SOLUTION

| | |
|---|---|
| Retinol Acetate | .00028 g/L |
| Riboflavin | .00002 g/L |
| Ribose | .001 g/L |
| Thiamine HCl | .00002 g/L |
| Thymine | .0006 g/L |
| Uracil | .0006 g/L |
| Xanthine.Na | .00069 g/L |
| Calcium chloride.$2H_2O$ | .265 g/L |
| Ferric Nitrate.$9H_2O$ | .00144 g/L |
| Magnesium sulfate (anhydrous) | 1.20 g/L |
| Potassium chloride | .4 g/L |
| Sodium Acetate (anhydrous) | .1 g/L |
| Sodium Chloride | 6.8 g/L |
| Sodium Phosphate Monobasic (anhydrous) | .244 g/L |
| Glucose | 2.0 g/L |
| Insulin | .01 g/L |
| Bovine serum albumin (BSA) | 30.0 g/L |
| $NaHCO_3$ | 4.4 g/L |
| Pyruvate | .22 g/L |
| Transferrin | .1 g/L |
| Serum | 100 ml |
| Impermeant (Cyclodextrin) | .5 g/L |
| Mucopolysaccharide (chondroitin sulfate B) | .004 g/L |
| ENDO GRO ™ (growth factor) | .20 g/L |
| heparin | .18 g/L |
| perfluorochemical emulsion* | 20% (v/v) |

*-as an oxygen carrier

As indicated in Table 1, a preferred oxygen carrier is a perfluorochemical such as perflubron emulsion (perfluoroocytl bromide, PFOB). Other perfluorochemical emulsions said to be useful as oxygen carrying agents are described, for example, in U.S. Pat. Nos. 5,403,575; 4,868,318; 4,866,096; 4,865,836; 4,686,024; 4,534,978; 4,443,480; 4,423,077; 4,252,827; 4,187,252; 4,186,253; 4,110,474; and 3,962,439. Such liquid PFC emulsions include, but are not limited to perfluorooctyl bromide, perfluorooctyl dibromide, bromofluorocarbons, perfluoroethers, Fluosol DA$^{TM}$, F-44E, 1,2-bisperfluorobutyl-ethylene, F-4-methyl octahydroquinol-idizine, 9 to 12 carbon perfluoro amines, perfluorodecalin, perfluoroindane, perfluorotrimethyl bicyclo[3,3,1] onane, perfluoromethyl adamante, perfluorodimethyl adamantane.

However, other oxygen carriers for providing oxygen during oxidative metabolism during preservation and treatment of the graft include, but are not limited to, hemoglobin, stabilized hemoglobin derivatives (made from hemolyzed human erythrocytes such as pyridoxylated hemoglobin), polyoxethylene conjugates (PHP) and recombinant hemoglobin products.

EXAMPLE 2

Methods For Monitoring Functional Characteristics

The warm preservation process/system to preserve organs ex vivo without traditional hypothermia (4°–10° C.) has been described in detail previously (U.S. Pat. Nos. 5,599,659 and 5,702,881 the disclosures of which are herein incorporated by reference). The process/system provides the necessary oxygen delivery, nutrients for metabolism, oncotic pressure, pH, perfusion pressures, and flow rates to support organ metabolism ex vivo, most often within or near the respective normal range in vivo. Further, the process/system supports a level of metabolism ex vivo which provides enough oxidative metabolism to result in the normal functional product of the organ. The development of this process/system which supports organs ex vivo, without traditional hypothermia, presents the opportunity to support a near normal rate of metabolism.

Using a perfusate of a known formulation, such as that illustrated in Table 1, can facilitate measurement of certain indicia of metabolic function, thus providing a means of assessing the function of the organ being perfused in the process/system. For example, the rate at which the glucose concentration is depleted, in relation to time, in the perfusate as it circulates through the organ, is a measure of organ function. Relative to a selected time point, a glucose concentration that is below the range of a normal level of glucose utilization may be an indicator of organ damage or inhibited metabolism. Another example of a measure of organ function is the amount of oxygen consumption as the perfusate circulates through the organ. Inadequate oxygen consumption, i.e. a low oxygen consumption compared to the normal range, may be indicative of tissue hypoxia. Yet another example of a measure of organ function is the vascular flow rate of perfusate circulating through the organ using a standard perfusion pressure. A low flow rate, compared to the normal range, may be indicative of vasoconstriction, edema, vascular endothelial cell swelling and loss of vascular integrity in a damaged organ.

The warm preservation process/system (20) includes machinery comprising a laminar or pulsatile pumping system, including means (22) for providing and controlling perfusion and the perfusion pressure; means for temperature control; and means for providing and controlling introduction of, and venting of, respiratory gases. With the method of the present invention, also provided in the warm technology process/system (20) is a device (10), such as a shunt that maintains the overall integrity of the process/system, which is operatively linked to the process/system to allow small test samples of perfusate to be diverted off line from the flow lines of perfusate which has already circulated through the organ and a means (12), such as a collection chamber, with which to collect the perfusate so diverted, so that measurements of the perfusate can be subsequently performed.

Figure 4:
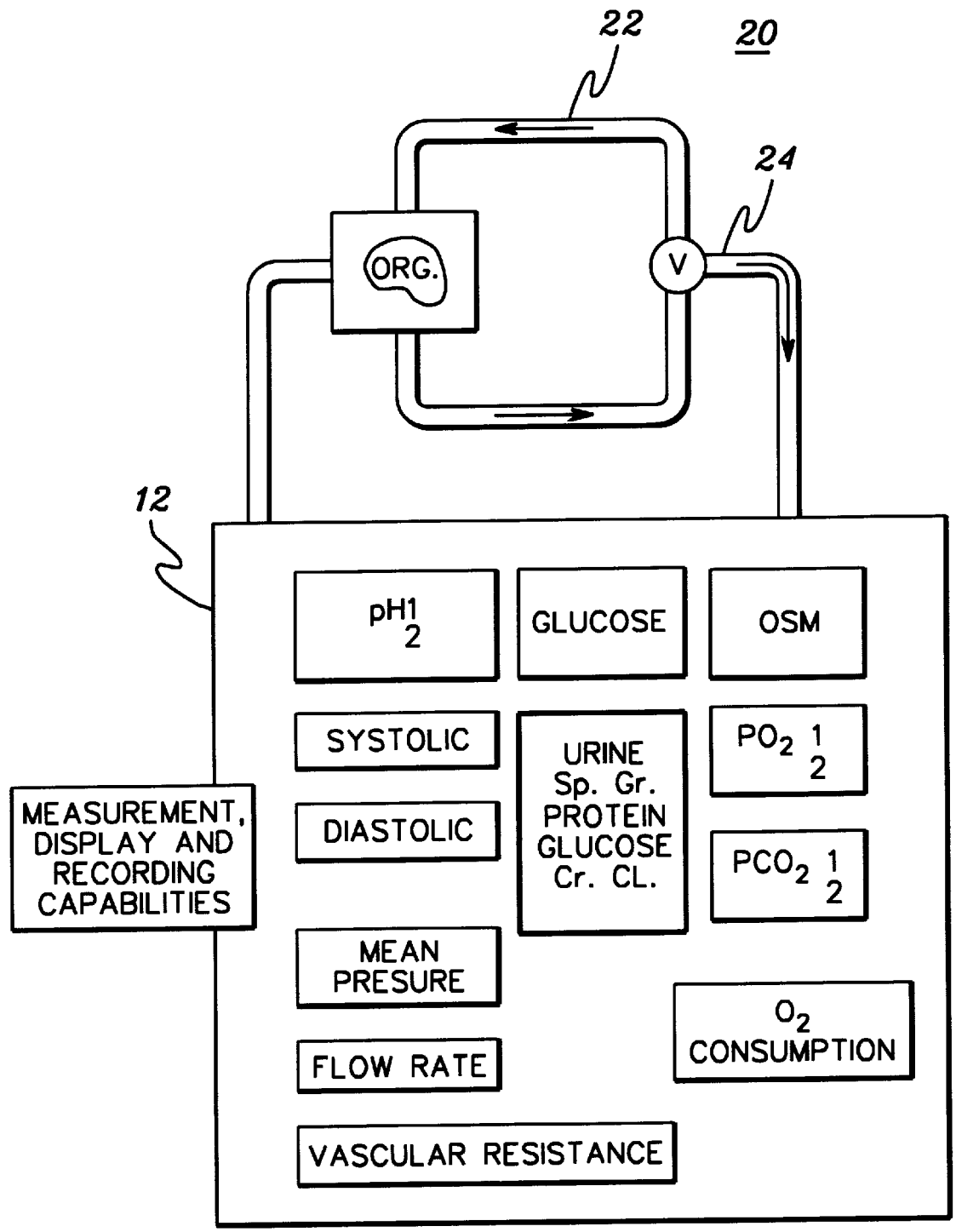
FIG. 4 is a schematic representing a pump design having the functional capabilities to enable the warm preservation process/system to make the measurements of the present invention.

In one embodiment, in-line measurements can be made of the constituents of the perfusate collected in the chamber. Thus, a new pump design comprises diagnostic means providing the warm preservation process/system with the capability to automatically monitor and measure one or more functional characteristics such as pH, various pressures, flow rate, vascular resistance, various chemical constituents, oxygenation, carbon dioxide concentration, and oxygen consumption (as diagrammed in FIG. 4), with display means to show measured values, and recording means to provide a record of such measurements. Methods known to those skilled in the art can be utilized for making the in-line measurements. For example, the chamber contents can be exposed to a bank of solid state micro-electrodes which generate electrical signals proportional to the chemical characteristics (U.S. Pat. No. 4,535,786) of the perfusate leaving the perfused organ. Alternatively, the chamber contents may be exposed to a spectroscopy instrument emitting and analyzing near-infrared as may be used to measure a constituent's concentration such as glucose concentration (U.S. Pat. No. 5,077,476). In another mode of this embodiment, the level of a constituent, such as glucose, may be measured by wavelength absorbance when tested by a light of known intensity. Another method for providing in-line measurement includes pumping the collected perfuste from the chamber to a clinical chemistry analyzer system which is adapted to the machinery (U.S. Pat. No.

4,786,394) comprising the warm preservation process/ system. Alternatively, the perfusate collected in the chamber may be removed from the chamber and measured by similar techniques in an "off-line" manner.

In another embodiment, the vascular flow rate of the perfusate circulating through the organ can be determined by using the means for diverting and collecting the circulated perfusate, by measuring the volume of perfusate collecting in the chamber in relation to time. As similar to the embodiment above, micro-electrodes may be used as a means to faciltate such determination of vascular flow rate.

Similarly, a second device means, such as a shunt or catheter operatively linked to the organ being perfused, may be used to divert organ product from the organ, such as urine from a kidney, and further comprises a means to collect the diverted organ product for subsequent measurement of parameters of the organ product which relate to organ function. Organ product can be measured in-line using the means and methods for measuring the chemical constituents known to those in the art; and means and methods for monitoring the flow rate and volume, as illustrated in the above embodiments. Alternatively, the organ product can be removed from the collection means and the product's constituents can be measured using similar techniques in an "off-line" manner.

EXAMPLE 3

Measurable Functional Characteristics in Kidneys Intended for Transplantation Overall renal function, as well as individual aspects of kidney physiology, can be determined by measuring concentrations of constituents in both the circulated perfusate, and the kidney product (urine). Thus, in accordance with the present invention, and with the methods and compositions in Examples 1 and 2, kidneys intended for transplantation may be prospectively assessed for metabolic function. Using the warm preservation process/system, kidneys intended for transplantation can be maintained at temperatures of 25°–32° C. for up to 18 hours at mean pressures ranging from 40–90 mmHg. This pressure range results in vascular flow rates of 80–150 cc/min. The renal perfusions are conducted at $PO_2$ of 170–185 torr to deliver oxygen at 7.7 ml/min. Under these conditions, examples of functional characteristics indicative of renal metabolism occurring at a temperature of 25° C. and 32° C., respectively, have been measured and are listed in Table 2 below:

TABLE 2

METABOLIC FUNCTION AFTER SIX HOURS OF EX VIVO PRESERVATION*

|  | Group 1: 25° C. | Group 2: 32° C. |
|---|---|---|
| $O_2$-consumption+ | 4.8 ml/min | 5.7 ml/min |
| diuresis | 143.1 cc/hr | 123.3 cc/hr |
| histology | normal | normal |
| perfusate glucose conc.** | 72 mg/dl | nd |

*specimens collected after 6 hours of perfusion and represents the mean from experimental data in each group
**starting glucose concentration: 165 mg/dl
+calculated using the method of Fick
nd not detectable within the threshold of testing In measuring one or more indicia of kidney function, there is a direct correlation between protein concentration and the rate of diuresis. The oncotic pressure of the process/system is an important regulator of the rate of diuresis. Oncotic pressure in the range of 2.5–4.0 g/dl provided the best quality diuresis in terms of cc/min, pH, and specific gravity (illustrated in FIG. 1, and in Table 4), whereas a higher oncotic pressure substantially diminished the diuresis. In the case of an oncotic pressure of approximately 8.0 g/dl, no urine was produced. Without any additives for oncotic pressure, an excessive diuresis occurred which resulted in a critical rise in the osmolality (Osm) of the circulating perfusate. Urine osmolality has a reference range of fron 300 to 900 mosmol/kgH$_2$O. Because osmolality is a measure of the number of dissolved solute particles in urine, a value outside the reference range (i.e. higher) may indicate damage to, or dysfunction of, the renal tubules (higher concentrations of dissolved substances such as glucose, sodium, and protein).

Another functional characteristic that can be measured and be indicative of renal function is tracer molecule clearance. This test involves measuring the volume of urine formed over a set time interval, and measuring the concentration of a tracer molecule (e.g., creatinine) in the urine and also measuring the concentration of that molecule in the circulated perfusate. The clearance value is used to determine glomerular filtration rate and/or secretory tubule function. If the renal function is normal, i.e. renal circulation is unimpaired, a molecule like creatinine is readily cleared from the perfusate into the urine. Impaired renal function may be indicated by an increase in the level of creatinine contained in the perfusate relative to the level in urine, thereby affecting the calculated clearance value. During ex vivo preservation using the described process/system, the delivery and consumption of oxygen was a critical factor in the creatinine clearance rate. Creatinine was added to the circulating perfusate at a concentration of 10 mg/dl. Suboptimal oxygen consumption resulted in a very low rate of creatinine cleared in the resulting urine. At very high levels of oxygen consumption, creatinine clearance in the urine produced, ex vivo with the described process/system, was demonstrated to be in the reference interval (normal range) of 40–100 mg/dl as shown in Table 3.

TABLE 3

| Oxygen consumption | Urine creatinine |
|---|---|
| 2.76 ml/min | 10 mg/dl |
| 4.71 ml/min | 48 mg/dl |
| 6.72 ml/min | 72 mg/dl |

The urine produced during the ex vivo preservation using the stated process/system, can be analyzed for specific functional characteristics, and in the ranges, such as those listed in Table 4. Specific gravity, relating to the number of solute particles, can be measured by an urinometer. The value reflects the concentrating ability of the kidney. Thus, a value outside (lower) than the reference interval may reflect renal tubular damage, since concentrating ability is one of the first functions to be lost as a result of renal tubular damage.

Measurement of pH reflects the amount of acid produced in the organ as a result of organ metabolism and oxidation. The regulation of the acid-base balance, together with the regeneration of free buffers, is ultimately a function of renal tubular cells. A urine pH which is more acidic than the reference interval, may indicate in renal tubular defects (i.e., defect in which $HCO_3^-$ is not reabsorbed from the urine). A urine pH which is more alkaline than the reference interval may indicate a renal tubular defect in which ions (i.e. $H^+$ or $K^+$) are not being reabsorbed from the urine. The presence of glucose or casts in the urine is an indicator of renal glomerular function.

TABLE 4

URINALYSIS

| | Measured values | Reference Interval |
|---|---|---|
| specific gravity | 1.010–1.013 | 1.010–1.020 |
| pH | 7.0–8.0 | 6.0–8.0 |
| diuresis | 0.5–8 cc/min | 1 cc/min minimum |
| glucose | negative | negative |
| casts | negative | negative |

Similarly, the function of the kidney, during the ex vivo preservation using the process/system, can be assessed for glomerular function by measuring protein in the urine, or other large molecules such as the oxygen carrier in the perfusate (i.e. perfluorochemical emulsion). The glomerular pores are lined with glycosylated proteins with strong negative electric charges. Since proteins are also negatively charged, the result is electrostatic repulsion; i.e these molecules are not normally present in the urine. However, where the glomerular filtration process is damaged, these substances may then be found in the urine as indicators of glomerular injury.

As discussed somewhat with creatinine clearance values, tubular function of the kidney may be assessed by the measurement of urinary creatinine. In functioning tubules, perfusate creatinine is secreted and not reabsorbed during urine production. Thus, creatinine is added to the perfusate as a tracer molecule to be detected by excretion in the urine.

Figure 2:
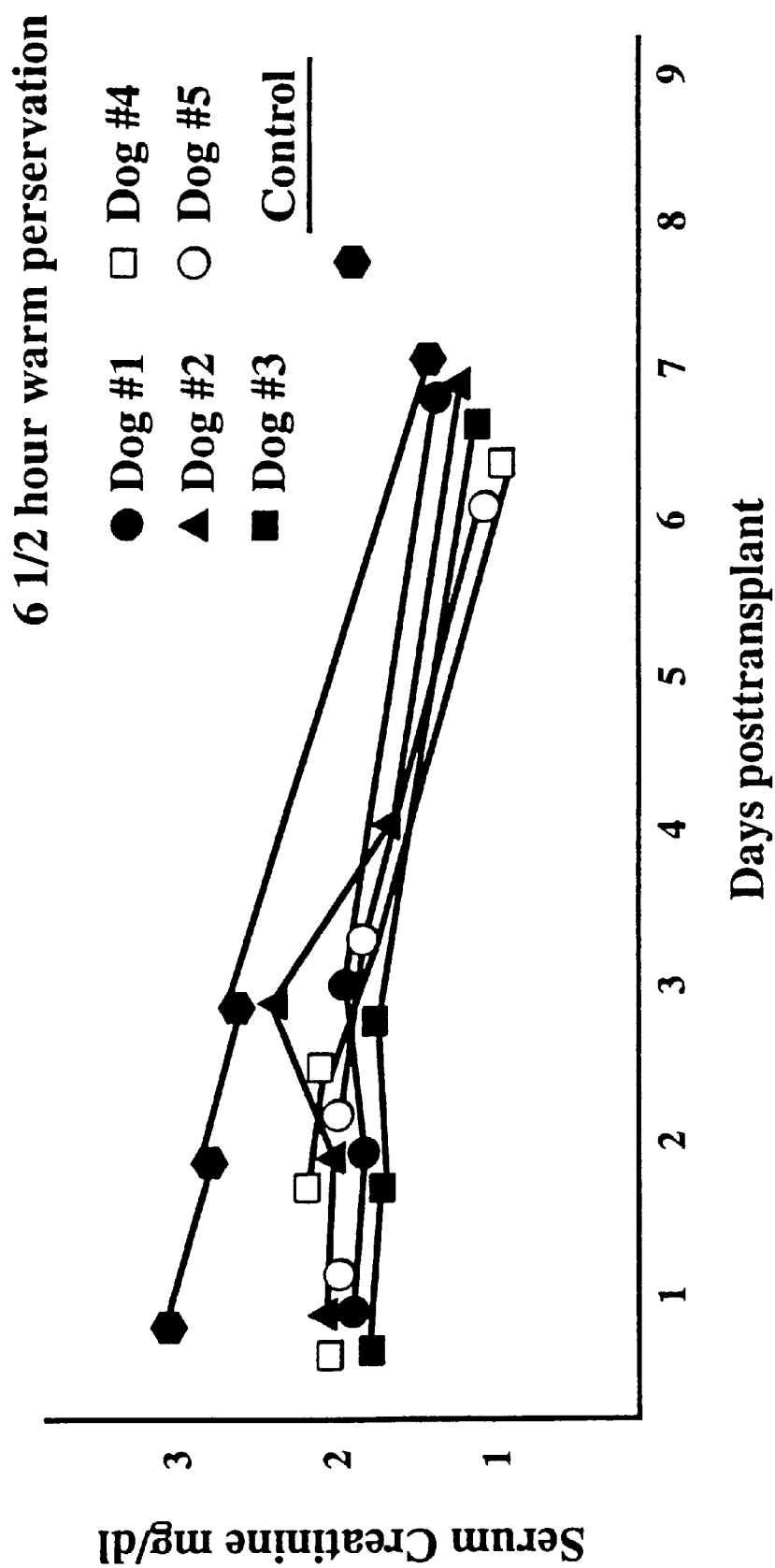
FIG. 2 is a graph representing successful autotransplantation and recipients' serum creatinine levels following storage for 6.5 hours using the ex vivo warm preservation process/system (○,●,□,■,Δ,▲) as compared to hypothermic storage with a perfusate solution for hypothermia (✲). Urine creatinine concentration measured at greater than 40.0 mg/dl, was found to correlate with, or be predictive of, successful posttransplantation renal function.
Figure 3:
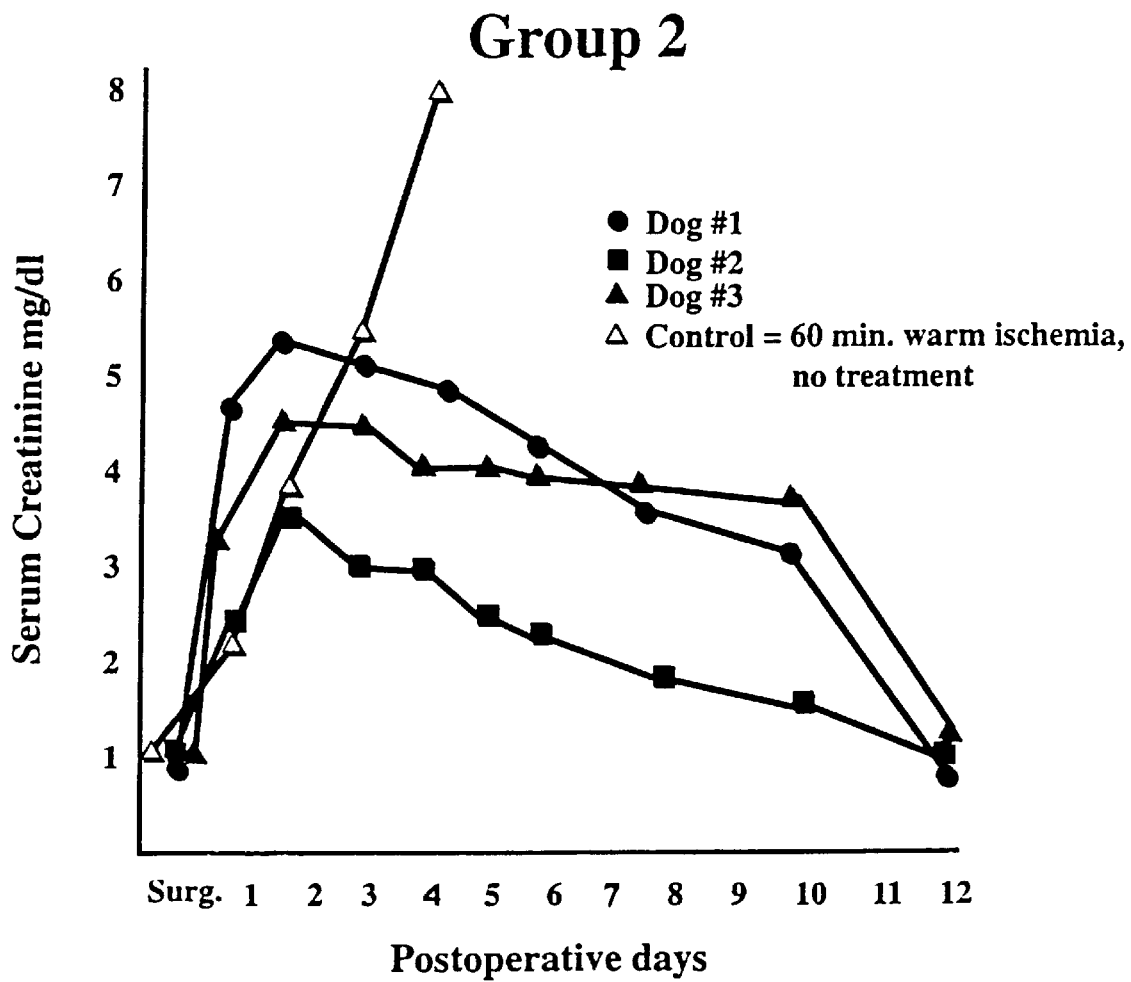
FIG. 3 is a graph representing autotransplantation with reversible acute tubular necrosis, and showing the recipients' serum creatinine levels following storage for 6.5 hours using the ex vivo warm preservation process/system (●,■, ▲) as compared to a control (Δ) which was 60 minutes of warm ischemia, no treatment. Urine creatinine concentration was measured at less than 40.0 mg/dl.

Those kidneys exhibiting good ex vivo functional characteristics with the described process/system were found to function well posttransplantation (See measured values, Table 4;& Group I, FIG. 2). For example, the urine was always found to be negative for protein and perfluorochemical emulsion leakage. The urinary creatinine concentration was always greater than 40 mg/dl. In contrast, poor functional characteristics i.e., protein or perfluorochemical leakage were associated with renal damage and poor posttransplantation course. In those kidneys exhibiting urinary creatinine concentrations of <40 mg/dl during ex vivo preservation with the described process/system the post-transplantation courses demonstrated an acute tubular necrosis indicative of poor graft function (Group 2, FIG. 3).

Additional means of assessing the function of the kidney being perfused in the process/system is the amount of oxygen consumption as the perfusate circulates, relative to a selected time interval, through the organ. Decreased oxygen consumption, i.e. a low oxygen consumption compared to the normal range, may be indicative of tissue hypoxia. Yet another example of a measure of organ function is the vascular flow rate of perfusate circulating through the kidney using a standard perfusion pressure relative to a selected time interval. A low flow rate, compared to the normal range, may be indicative of edema, vasoconstriction, vascular endothelial cell swelling and loss of vascular integrity in a damaged kidney.

Thus, measurement of functional characteristics in organs preserved in the warm preservation process/system, i.e. evaluating functional characteristics of metabolism of an organ intended for transplantation, can be a means to prospectively assess organ function posttransplantation. By measuring parameters of organ product and/or circulated perfusate during ex vivo warm preservation, and relating values of the measured parameters to reference interval values, values of one or more measured parameters outside the reference intervals may be indicia of organ damage, injury, or poor functional capabilities which may affect the function of the organ posttransplantation. The prospective assessment may be useful in the evaluation of the functional status of: a graft after cold or warm ischemia; in a borderline donor (as discussed previously); or in any case where the kidney may have been compromised. The acceptable level of ex vivo function will be determined by the respective clinicians as the range yielding the threshold of clinical function acceptable at each transplant center.

EXAMPLE 4

Measurable Functional Characteristics in Liver Intended for Transplantation

Overall liver function, as well as individual aspects of physiology of the liver, can be determined by measuring concentrations of constituents in both the circulated perfusate, and the liver product (bile). Thus, in accordance with the present invention, and with the methods and compositions as illustrated in Examples 1–3, liver intended for transplantation may be prospectively assessed for metabolic function.

Functional characteristics of liver can be assessed by measuring parameters including, but not limited to, bile concentrations of bile salts, cholesterol, alkaline phosphatase; bile pH; and liver vascular flow rate, oxygen consumption, and glucose utilization (as measured from the perfusate).

In particular, elevated levels of alkaline phosphatase, as measured in the bile and/or in the perfusate (i.e., above the reference interval determined by the respective clinician) may be an indicator of hepatic or hepatobilliary disease. Concurrent with the measurement of perfusate alkaline phosphatase (ALP) levels, it may be useful to determine perfusate levels of leucine aminopeptidase (LAP) and gamma glutamyl transferase (GGT) which appear to parellel increases of ALP in hepatobiliary disease.

Additional means of assessing the function of a liver being perfused in the process/system, is the amount of oxygen consumption as the perfusate circulates through the organ, relative to a selected time interval. Decreased oxygen consumption, i.e. a low oxygen consumption compared to the normal range, may be indicative of tissue hypoxia. Yet another example of a measure of organ function is the vascular flow rate of perfusate circulating through the liver using a standard perfusion pressure. A low flow rate, compared to the normal range determined by the respective clinician, may be indicative of vasoconstriction, edema, vascular endothelial cell swelling and loss of vascular integrity in a damaged liver. The acceptable level of ex vivo function will be determined by the respective clinicians as the range yielding the threshold of clinical function acceptable at each transplant center.

EXAMPLE 5

Measurable Functional Characteristics in Pancreas Intended for Transplantation

Overall pancreas function, as well as individual aspects of physiology of the pancreas, can be determined by measuring concentrations of constituents in both the circulated perfusate, and the pancreas. Thus, in accordance with the present invention, and with the methods and compositions as illustrated in Examples 1–3, pancreas intended for transplantation may be prospectively assessed for metabolic function.

Functional characteristics of pancreas can be assessed by measuring parameters including, but not limited to, pancreatic enzyme concentrations such as amylase, lipase; the hormone insulin; pancreatic secretion pH, sodium and potassium; and pancreas vascular flow rate, oxygen consumption, and glucose utilization (as measured from the perfusate).

In particular, altered activity of amylase and lipase, as measured in the pancreatic juice and/or in the perfusate (i.e., above the reference interval determined by the respective clinician; for example, perfusate amylase actvity reference level may be 70–300 U/l and lipase activity reference level up to 10 U/ml, depending on the method used to measure activity) may be an indicator of pancreatitis.

Additional means of assessing the function of a pancreas being perfused in the process/system, is the amount of oxygen consumption as the perfusate circulates through the organ, relative to a selected time interval. Decreased oxygen consumption, i.e. a low oxygen consumption compared to the normal range, may be indicative of tissue hypoxia. Yet another example of a measure of organ function is the vascular flow rate of perfusate circulating through the pancreas using a standard perfusion pressure. A low flow rate, compared to the normal range determined by the respective clinician, may be indicative of vasoconstriction, edema, vascular endothelial cell swelling and loss of vascular integrity in a damaged pancreas. The acceptable level of ex vivo function will be determined by the respective clinicians as the range yielding the threshold of clinical function acceptable at each transplant center.

EXAMPLE 6

Measurable Functional Characteristics in Heart Intended for Transplantation

Overall heart function, as well as individual aspects of physiology of the heart, can be determined by measuring concentrations of constituents in both the circulated perfusate, and the heart. Thus, in accordance with the present invention, and with the methods and compositions as illustrated in Examples 1–3, heart intended for transplantation may be prospectively assessed for metabolic function. To illustrate this embodiment, rat hearts were preserved ex vivo at 32° C. for 6 hours using the warm preservation process. The hearts were perfused via a cannula in the aorta at mean pressures ranging from 35–60 mmHg. This pressure range resulted in vascular flow rates of 4–6 cc/min/gm. The heart perfusions were conducted at $PO_2$ of 200–250 torr to deliver adequate amounts of oxygen. Under these conditions, examples of functional characteristics supported by the heart metabolism are listed in Table 5 below.

TABLE 5

Measurable Function in Hearts Intended for Transplantation*

| | Preservation Times | | |
|---|---|---|---|
| | 2 hrs (n = 6) | 4 hrs (n = 6) | 6 hrs (n = 6) |
| mechanical work beats/min | 34 | 36 | 36 |
| electrical activity | QRS complexes | QRS complexes | QRS complexes |

*expressed as the mean of the experimental data in each group

Throughout the ex vivo period of preservation, the rat hearts gave evidence of mechanical work. The hearts spontaneously beat with heart rates of 34–36 beats/min. Throughout the period of ex vivo preservation the electrocardiogram (ECG) revealed continuous electrical activity in the heart allografts. The donor sinus node function is responsible for electrical activity in these denervated hearts. All attributes to the P wave were present and no drug support was given during the period of ex vivo preservation. Similarly, throughout this period no electrical pacing was attempted.

The presence of both mechanical and electrical activity in the rat hearts during the entire period of ex vivo preservation at 32° C. were predictive of function upon allotranplantation. Following 6 hours of ex vivo preservation and functional evaluation, the hearts were transplanted. The preserved hearts were heterotopically transplanted into the abdomens of recipient rats. Those hearts demonstrating stable mechanical and electrical activity during the period of ex vivo preservation, beat spontaneously upon reperfusion following transplantation. No mechanical or electrical defibrillation was required. In these hearts, the strength and regularity of the beats rapidly increased within minutes of reperfusion (Table 6). The hearts continued to beat throughout the posttransplant period. Normal QRS complexes were found within twenty minutes of reperfusion. Upon euthanasia the histologic evaluations indicated well preserved myocardium with well maintained coronary arteries and microvessels.

The hearts demonstrating irregular mechanical and electrical activity during the period of ex vivo preservation functioned poorly upon reperfusion following transplantation. In all three cases, the hearts did not spontaneously beat upon reperfusion and required mechanical defibrillation. In all cases where the ex vivo function during preservation was poor, following reperfusion and transplantation, the hearts demonstrated poor function (Table 6). Abnormal QRS complexes were found following cardioversion. Histologic evaluations indicated areas of myocardial damage.

TABLE 6

Posttransplantation Function

| | Stable Parameters (n = 6) | Irregular Parameters (n = 3) |
|---|---|---|
| Reperfusion | Immediate | Slow |
| Spontaneous Beating | Yes | No |
| ECG | normal QRS complexes | abnormal QRS complexes |
| Histology of myocardium | well preserved | areas of damage |

Functional characteristics of heart can be assessed by measuring parameters including, but not limited to, heart enzymes such as transaminases (aspartate aminotransferase, AST), lactate dehydrogenase (LD), fructose 1,6-diphosphate aldolase (ALS), malate dehydrogenase (MD), glutathione reductase (GR), creatine phosphokinase (CPK), hydroxybutyrate dehydrogenase (HBD); heart vascular flow rate, oxygen consumption, and glucose utilization (as measured from the perfusate).

Indicators of cardiovascular disease may include increased levels of AST, LD, ALS, MD, GR, CPK and HBD in circulated perfusate relative to reference levels determined by the respective clinician (exs. of reference levels include AST: <20 U/l; and LD: 0–300 U/L).

Additional means of assessing the function of a heart being perfused in the process/system, is the amount of oxygen consumption as the perfusate circulates through the organ, relative to a selected time interval. Decreased oxygen consumption, i.e. a low oxygen consumption compared to the normal range, may be indicative of tissue hypoxia. Yet another example of a measure of organ function is the vascular flow rate of perfusate circulating through the heart using a standard perfusion pressure. A low flow rate, compared to the normal range determined by the respective clinician, may be indicative of vasoconstriction, edema, vascular endothelial cell swelling and loss of vascular integrity in a damaged heart. The acceptable level of ex vivo function will be determined by the respective clinicians as the range yielding the threshold of clinical function acceptable at each transplant center.

Also, heart function can be assessed by measuring the electric potential of the heart, being perfused by the warm preservation process/system, such as by electrocardiogram using standard methods known to those skilled in the art. From an electrocardiogram can be determined abnormal patterns (determined from the wave pattern) which may be characteristic of infarction, ischemia, and hypertrophy; and which may be predictive of poor functional performance of the heart posttransplantation.

EXAMPLE 7

Measurable Functional Characteristics in Small Bowel Intended for Transplantation Overall bowel function, as well as individual aspects of physiology of the small bowel, can be determined by measuring concentrations of constituents in both the circulated perfusate, and the small bowel. Thus, in accordance with the present invention, and with the methods and compositions as illustrated in Examples 1–3, small bowel intended for transplantation may be prospectively assessed for metabolic function.

Functional characteristics of small bowel can be assessed by measuring parameters including, but not limited to, functional assays such as gastric acid stimulation tests, and absorption assays using tracer molecules; small bowel vascular flow rate, oxygen consumption, and glucose utilization (as measured from the perfusate).

A gastric stimulation test is performed by first taking a basal sample of gastric secretions, i.e. before attempting to stimulate gastric secretion by the addition of a stimulant to the perfusate. Known stimulants, and methods of use thereof, of gastric secretion include histamine, pentagastrin, histalog, and insulin(-induced hypoglycemia). Stimulation tests showing anacidity may indicate a damaged or injured small bowel. An absorption test involves introducing directly into the small bowel a substance that is capable of being traced because of a diagnostic marker associated with the substance. Then, either the contents of the small bowel can be systematically analyzed over time for disappearance of the tracer molecule, or the perfusate can be measured for the appearance of the tracer molecule, to measure the ability of the small bowel to absorb substances. Impaired absorption may be indicative of a damaged or injured small bowel.

Additional means of assessing the function of small bowel being perfused in the process/system, is the amount of oxygen consumption as the perfusate circulates through the organ, relative to a selected time interval. Decreased oxygen consumption, i.e. a low oxygen consumption compared to the normal range, may be indicative of tissue hypoxia. Yet another example of a measure of organ function is the vascular flow rate of perfusate circulating through the small bowel using a standard perfusion pressure. A low flow rate, compared to the normal range determined by the respective clinician, may be indicative of vasoconstriction, edema, vascular endothelial cell swelling and loss of vascular integrity in a damaged small bowel. The acceptable level of ex vivo function will be determined by the respective clinicians as the range yielding the threshold of clinical function acceptable at each transplant center.

It should be understood that the embodiments and the examples of the present invention, as described herein, are for purposes of illustration only, and not limitation, and any changes or modifications as will become apparent to one of ordinary skill in the art from the foregoing description and accompanying figures are intended to be included within the scope of the appended claims and the equivalents thereof.

What is claimed is:

1. A device which is operatively linked to an ex vivo warm preservation system having flow lines and a non-blood perfusate circulating through said flow lines wherein said system performs a process of perfusing and preserving an organ ex vivo at near normal metabolism, wherein said device comprises:

(a) means for diverting from the flow lines a sample of perfusate which has already circulated through the organ, while maintaining the overall integrity of the perfusion process; and (b) means for collecting the perfusate so that measurements of the perfusate can be subsequently performed.

2. The device of claim 1, further comprising a means in communication with said collecting means for making measurements of the collected perfusate; display means, in communication with said measurement means showing values of said measurements; and recording means, in communication with said measurement means, for making a record of said measurements.

3. The device of claim 2 wherein said measurements of the collected perfusate are indicative of organ function.

4. A device operatively linked to an ex vivo warm preservation system wherein said system performs a process of preserving an organ ex vivo by perfusing said organ with a non-blood perfusate, at near normal metabolism, wherein said device comprises a means of diverting off organ product from the organ, while maintaining the overall integrity of the perfusion process, and a collection means to collect the organ product so that measurements of the organ product can be subsequently performed.

5. The device of claim 4, further comprising a means in communication with said collection means for making measurements of the collected organ product; display means in communication with said measurements means showing values of said measurements; and recording means in communication with said measurements means for making a record of said measurements.

6. The device of claim 5, wherein said measurements of the collected organ product are indicative of organ function.

* * * * *

UNITED STATES PATENT AND TRADEMARK OFFICE
CERTIFICATE OF CORRECTION

PATENT NO. : 6,024,698
DATED : February 15, 2000
INVENTOR(S) : Lauren Brasile

It is certified that error appears in the above-identified patent and that said Letters Patent is hereby corrected as shown below:

IN THE TITLE: Item [54]

Line 4, delete "TRANSPLANTATIONS" and replace with --TRANSPLANTATION--.

IN THE ABSTRACT: Item [57]

Line 8, after "perfusate", insert --so--.

Col. 8, line 32, after "device (10)", insert --including means (24)--.

Signed and Sealed this

Second Day of January, 2001

Attest:

Attesting Officer

Q. TODD DICKINSON

Commissioner of Patents and Trademarks